(12) United States Patent
Zhang et al.

(10) Patent No.: US 10,857,210 B2
(45) Date of Patent: Dec. 8, 2020

(54) COMPOSITIONS AND METHODS TO PROMOTE WOUND HEALING

(71) Applicant: Wayne State University, Detroit, MI (US)

(72) Inventors: Kezhong Zhang, Canton, MI (US); Jiemei Wang, Troy, MI (US)

(73) Assignee: Wayne State University, Detroit, MI (US)

(*) Notice: Subject to any disclaimer, the term of this patent is extended or adjusted under 35 U.S.C. 154(b) by 99 days.

(21) Appl. No.: 15/203,628

(22) Filed: Jul. 6, 2016

(65) Prior Publication Data

US 2017/0007678 A1    Jan. 12, 2017

Related U.S. Application Data

(60) Provisional application No. 62/189,102, filed on Jul. 6, 2015.

(51) Int. Cl.

| | |
|---|---|
| *A61K 38/45* | (2006.01) |
| *A61K 9/00* | (2006.01) |
| *A61K 9/12* | (2006.01) |
| *A61K 9/06* | (2006.01) |
| *A61K 38/17* | (2006.01) |
| *A61K 9/14* | (2006.01) |

(52) U.S. Cl.
CPC ............ *A61K 38/45* (2013.01); *A61K 9/0014* (2013.01); *A61K 9/06* (2013.01); *A61K 9/12* (2013.01); *A61K 9/141* (2013.01); *A61K 38/1709* (2013.01); *C12Y 207/11001* (2013.01); *C12N 2710/10343* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2003/0180259 A1* | 9/2003 | Brem ................ | A61K 38/1866 424/93.2 |
| 2007/0248641 A1 | 10/2007 | Yang et al. | |
| 2012/0202751 A1* | 8/2012 | Koong ............... | A01K 67/0275 514/20.1 |
| 2013/0184323 A1 | 7/2013 | Benbrook et al. | |
| 2013/0218143 A1 | 8/2013 | Ross | |
| 2015/0030681 A1 | 1/2015 | Merry et al. | |
| 2015/0307843 A1 | 10/2015 | Huang et al. | |

FOREIGN PATENT DOCUMENTS

| | | | | |
|---|---|---|---|---|
| WO | WO-2009079451 A2 * | 6/2009 | ........... | C07K 14/522 |
| WO | WO2011019757 | 2/2011 | | |

OTHER PUBLICATIONS

Kay Nature review, 346-358 (Year: 2003).*
Branski et al Gene Therapy 14, 1-10 (Year: 2007).*
Gorell Cold Spring Harb Perspect Med 4: 1-15 (Year: 2014).*
Falanga Lancet 366: 1736-43 (Year: 2005).*
Sarkar A MIT, Thesis (S.M.)—Massachusetts Institute of Technology, Dept. of Mechanical Engineering, hdl.handle.net/1721.1/45215 , pp. 1-161, abstract (Year: 2008).*
Zeng et al Circulation. 127: 1712-1722 (Year: 2013).*
Barbhaiya et al J. Am. Coll. Surg., vol. 215, No. 3, Suppl, S85 (Year: 2012).*
Bonadio et al J. Mod. Med, 78, 303-311 (Year: 2000).*
Elliot et al Journal of Investigative Dermatology 138, 736-740 (Year: 2018).*
Scherer et al Wounds 20(1), 18-28, 1-12 (Year: 2008).*
Young et al J Pathol. 208:299-318 (Year: 2006).*
Barbhaiya, et al., "Xbp1 inhibition delays wound healing by inhibition of cell migration and proliferation," J. Am. Coll. Surg., vol. 215, No. 3, Suppl, 2012, p. S85.
Bonadio, "Local Gene Delivery for Tissue Regeneration," M. Regener. Med., vol. 1, 2000, pp. 25-29.
Butler, et al., "Unfolded Protein Response Regulation in Keloid Cells", J. Surg. Res., vol. 167, No. 1, 2011, pp. 151-157.
Heinemann, et al., "Delivery of proteins to mammalian cells via gold nanoparticle mediated laser transfection," Nanotechnology, vol. 25, No. 24, 2014, p. 245101.
Qiu, et al., "Toll-like receptor-mediated IRE1alpha activation as a therapeutic target for inflammatory arthritis," EMBO J., vol. 32, No. 18, 2013, pp. 2477-2490.
Schurmann, et al., "Deregulated unfolded protein response in chronic wounds of diabetic ob/ob mice: a potential connection to inflammatory and angiogenic disorders in diabetes-impaired wound healing," Biochem Biophys. Res. Commun., vol. 446, No. 1, 2014, pp. 195-200.
Silvestre, "Vascular Endothelial Growth Factor and Angiogenesis The Xbp1 Games," Circulation, vol. 127, No. 16, 2013, pp. 1644-1646.
Wang, et al., "MicroRNA miR-27b rescues bone marrow-derived angiogenic cell function and accelerates wound healing in type 2 diabetes mellitus," Arterioscler. Thromb. Vasc. Biol., vol. 34, 2014, pp. 99-109.
Zeng, et al., "Vascular Endothelial Cell Growth-Activated XBP1 Splicing in Endothelial Cells Is Crucial for Angiogenesis," Circulation, vol. 127, No. 16, 2013, pp. 1712-1722.
Barrientos et al., "Clinical Application of Growth Factors and Cytokines in Wound Healing," Wound Repair Regen., vol. 22, 2014, pp. 569-578.

(Continued)

*Primary Examiner* — Anoop K Singh
(74) *Attorney, Agent, or Firm* — Lee & Hayes, P.C.; Tanya M. Harding; C. Rachal Winger

(57) ABSTRACT

Compositions and methods to promote wound healing are described. The compositions and methods up-regulate X-box binding protein 1 (XBP1) and/or inositol-requiring enzyme-1 (IRE-1). In various embodiments, the compositions and methods can be used to promote wound healing in diabetic subjects.

6 Claims, 11 Drawing Sheets

Specification includes a Sequence Listing.

(56) References Cited

OTHER PUBLICATIONS

Embil et al., "Recombinant Human Platelet-Derived Growth Factor-BB (Becaplermin) for Healing Chronic Lower Extremity Diabetic Ulcers: An Open-Label Clinical Evaluation of Efficacy," Wound Repair Regen., vol. 8, No. 3, 2000, pp. 162-168.
Galiano et al., "Topical Vascular Endothelial Growth Factor Accelerates Diabetic Wound Healing Through Increased Angiogenesis and by Mobilizing and Recruiting Bone Marrow-Derived Cells," Am. J. Pathol., vol. 164, No. 6, 2004, pp. 1935-1947.
Kim et al., "Antagonism of VEGF-A-Induced Increase in Vascular Permeability by an Integrin alpha3beta1-Shp-1-cAMP/PKA Pathway," Blood, vol. 120, No. 24, 2012, pp. 4892-4902.
Smiell et al., "Efficacy and Safety of Becaplermin (Recombinant Human Platelet-Derived Growth Factor-BB) in Patients with Nonhealing, Lower Extremity Diabetic Ulcers: A Combined Analysis of Four Randomized Studies," Wound Repair Regen., vol. 7, No. 5, 1999, pp. 335-346.
Steed, "Clinical Evaluation of Recombinant Human Platelet-Derived Growth Factor for the Treatment of Lower Extremity Diabetic Ulcers," Diabetic Ulcer Study Group, J. Vasc. Surg., vol. 21, No. 1, 1995, pp. 71-81.

\* cited by examiner

FIG. 11

Human XBP1 Amino Acid Sequence

MVVVAAAPNPADGTPKVLLLSGQPASAAGAPAGQALPLMVPAQRGASPEAASGGLP
QARKRQRLTHLSPEEKALRRKLKNRVAAQTARDRKKARMSELEQQVVDLEEENQKLL
LENQLLREKTHGLVVENQELRQRLGMDALVAEEEAEAKGNEVRPVAGSAESAALRLR
APLQQVQAQLSPLQNISPWILAVLTLQIQSLISCWAFWTTWTQSCSSNALPQSLPAWR
SSQRSTQKDPVPYQPPFLCQWGRHQPSWKPLMN (SEQ ID NO: 1)

Human IRE-1 Amino Acid Sequence

MPARRLLLLLTLLLPGLGIFGSTSTVTLPETLLFVSTLDGSLHAVSKRTGSIKWTLKEDP
VLQVPTHVEEPAFLPDPNDGSLYTLGSKNNEGLTKLPFTIPELVQASPCRSSDGILYMG
KKQDIWYVIDLLTGEKQQTLSSAFADSLCPSTSLLYLGRTEYTITMYDTKTRELRWNAT
YFDYAASLPEDDVDYKMSHFVSNGDGLVVTVDSESGDVLWIQNYASPVVAFYVWQRE
GLRKVMHINVAVETLRYLTFMSGEVGRITKWKYPFPKETEAKSKLTPTLYVGKYSTSLY
ASPSMVHEGVAVVPRGSTLPLLEGPQTDGVTIGDKGECVITPSTDVKFDPGLKSKNKL
NYLRNYWLLIGHHETPLSASTKMLERFPNNLPKHRENVIPADSEKKSFEEVINLVDQTS
ENAPTTVSRDVEEKPAHAPARPEAPVDSMLKDMATIILSTFLLIGWVAFIITYPLSMHQQ
QQLQHQQFQKELEKIQLLQQQQQQLPFHPPGDTAQDGELLDTSGPYSESSGTSSPST
SPRASNHSLCSGSSASKAGSSPSLEQDDGDEETSVVIVGKISFCPKDVLGHGAEGTIV
YRGMFDNRDVAVKRILPECFSFADREVQLLRESDEHPNVIRYFCTEKDRQFQYIAIELC
AATLQEYVEQKDFAHLGLEPITLLQQTTSGLAHLHSLNIVHRDLKPHNILISMPNAHGKIK
AMISDFGLCKKLAVGRHSFSRRSGVPGTEGWIAPEMLSEDCKENPTYTVDIFSAGCVF
YYVISEGSHPFGKSLQRQANILLGACSLDCLHPEKHEDVIARELIEKMIAMDPQKRPSA
KHVLKHPFFWSLEKQLQFFQDVSDRIEKESLDGPIVKQLERGGRAVVKMDWRENITVP
LQTDLRKFRTYKGGSVRDLLRAMRNKKHHYRELPAEVRETLGSLPDDFVCYFTSRFP
HLLAHTYRAMELCSHERLFQPYYFHEPPEPQPPVTPDAL (SEQ ID NO: 2)

SEQUENCE LISTING

<160> NUMBER OF SEQ ID NOS: 2

<210> SEQ ID NO 1
<211> LENGTH: 261
<212> TYPE: PRT
<213> ORGANISM: Homo sapien

<400> SEQUENCE: 1

Met Val Val Val Ala Ala Ala Pro Asn Pro Ala Asp Gly Thr Pro Lys
 1               5                  10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
            180                 185                 190

Val Leu Thr Leu Gln Ile Gln Ser Leu Ile Ser Cys Trp Ala Phe Trp
        195                 200                 205

Thr Thr Trp Thr Gln Ser Cys Ser Ser Asn Ala Leu Pro Gln Ser Leu
    210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260

<210> SEQ ID NO 2
<211> LENGTH: 977
<212> TYPE: PRT
<213> ORGANISM: Homo sapien

<400> SEQUENCE: 2

```
Met Pro Ala Arg Arg Leu Leu Leu Leu Thr Leu Leu Pro Gly
1               5                   10                  15

Leu Gly Ile Phe Gly Ser Thr Ser Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65              70                  75                  80

Ser Leu Tyr Thr Leu Gly Ser Lys Asn Asn Glu Gly Leu Thr Lys Leu
            85                  90                  95

Pro Phe Thr Ile Pro Glu Leu Val Gln Ala Ser Pro Cys Arg Ser Ser
        100                 105                 110

Asp Gly Ile Leu Tyr Met Gly Lys Lys Gln Asp Ile Trp Tyr Val Ile
    115                 120                 125

Asp Leu Leu Thr Gly Glu Lys Gln Gln Thr Leu Ser Ser Ala Phe Ala
130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
            165                 170                 175

Ala Thr Tyr Phe Asp Tyr Ala Ala Ser Leu Pro Glu Asp Asp Val Asp
        180                 185                 190

Tyr Lys Met Ser His Phe Val Ser Asn Gly Asp Gly Leu Val Val Thr
    195                 200                 205

Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
            245                 250                 255

Ser Gly Glu Val Gly Arg Ile Thr Lys Trp Lys Tyr Pro Phe Pro Lys
        260                 265                 270

Glu Thr Glu Ala Lys Ser Lys Leu Thr Pro Thr Leu Tyr Val Gly Lys
    275                 280                 285

Tyr Ser Thr Ser Leu Tyr Ala Ser Pro Ser Met Val His Glu Gly Val
290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
            325                 330                 335

Ser Thr Asp Val Lys Phe Asp Pro Gly Leu Lys Ser Lys Asn Lys Leu
        340                 345                 350

Asn Tyr Leu Arg Asn Tyr Trp Leu Leu Ile Gly His His Glu Thr Pro
    355                 360                 365

Leu Ser Ala Ser Thr Lys Met Leu Glu Arg Phe Pro Asn Asn Leu Pro
370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
            405                 410                 415
```

```
Thr Val Ser Arg Asp Val Glu Lys Pro Ala His Ala Pro Ala Arg
            420                 425             430

Pro Glu Ala Pro Val Asp Ser Met Leu Lys Asp Met Ala Thr Ile Ile
        435                 440                 445

Leu Ser Thr Phe Leu Leu Ile Gly Trp Val Ala Phe Ile Ile Thr Tyr
    450                 455                 460

Pro Leu Ser Met His Gln Gln Gln Leu Gln His Gln Gln Phe Gln
465             470                 475                 480

Lys Glu Leu Glu Lys Ile Gln Leu Leu Gln Gln Gln Gln Gln Leu
            485                 490                 495

Pro Phe His Pro Pro Gly Asp Thr Ala Gln Asp Gly Glu Leu Leu Asp
        500                 505                 510

Thr Ser Gly Pro Tyr Ser Glu Ser Ser Gly Thr Ser Ser Pro Ser Thr
        515                 520                 525

Ser Pro Arg Ala Ser Asn His Ser Leu Cys Ser Gly Ser Ser Ala Ser
    530                 535                 540

Lys Ala Gly Ser Ser Pro Ser Leu Glu Gln Asp Asp Gly Asp Glu Glu
545             550                 555                 560

Thr Ser Val Val Ile Val Gly Lys Ile Ser Phe Cys Pro Lys Asp Val
                565                 570                 575

Leu Gly His Gly Ala Glu Gly Thr Ile Val Tyr Arg Gly Met Phe Asp
            580                 585                 590

Asn Arg Asp Val Ala Val Lys Arg Ile Leu Pro Glu Cys Phe Ser Phe
    595                 600                 605

Ala Asp Arg Glu Val Gln Leu Leu Arg Glu Ser Asp Glu His Pro Asn
        610                 615                 620

Val Ile Arg Tyr Phe Cys Thr Glu Lys Asp Arg Gln Phe Gln Tyr Ile
625             630                 635                 640

Ala Ile Glu Leu Cys Ala Ala Thr Leu Gln Glu Tyr Val Glu Gln Lys
            645                 650                 655

Asp Phe Ala His Leu Gly Leu Glu Pro Ile Thr Leu Leu Gln Gln Thr
        660                 665                 670

Thr Ser Gly Leu Ala His Leu His Ser Leu Asn Ile Val His Arg Asp
    675                 680                 685

Leu Lys Pro His Asn Ile Leu Ile Ser Met Pro Asn Ala His Gly Lys
        690                 695                 700

Ile Lys Ala Met Ile Ser Asp Phe Gly Leu Cys Lys Lys Leu Ala Val
705             710                 715                 720

Gly Arg His Ser Phe Ser Arg Arg Ser Gly Val Pro Gly Thr Glu Gly
            725                 730                 735

Trp Ile Ala Pro Glu Met Leu Ser Glu Asp Cys Lys Glu Asn Pro Thr
        740                 745                 750

Tyr Thr Val Asp Ile Phe Ser Ala Gly Cys Val Phe Tyr Tyr Val Ile
    755                 760                 765

Ser Glu Gly Ser His Pro Phe Gly Lys Ser Leu Gln Arg Gln Ala Asn
        770                 775                 780

Ile Leu Leu Gly Ala Cys Ser Leu Asp Cys Leu His Pro Glu Lys His
785             790                 795                 800

Glu Asp Val Ile Ala Arg Glu Leu Ile Glu Lys Met Ile Ala Met Asp
            805                 810                 815

Pro Gln Lys Arg Pro Ser Ala Lys His Val Leu Lys His Pro Phe Phe
        820                 825                 830
```

```
Trp Ser Leu Glu Lys Gln Leu Gln Phe Phe Gln Asp Val Ser Asp Arg
        835                 840                 845

Ile Glu Lys Glu Ser Leu Asp Gly Pro Ile Val Lys Gln Leu Glu Arg
    850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
        930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Pro Val Thr Pro Asp Ala
                965                 970                 975

Leu
```

COMPOSITIONS AND METHODS TO PROMOTE WOUND HEALING

CROSS REFERENCE TO RELATED APPLICATION

This application claims priority to U.S. Provisional Patent Application No. 62/189,102 filed on Jul. 6, 2015, which is incorporated herein by reference in its entirety as if fully set forth herein.

STATEMENT OF GOVERNMENT INTEREST

This invention was made with government support under contract DK090313 awarded by National Institutes of Health and contract AR066634 awarded by the National Institutes of Health. The government has certain rights in the invention.

SEQUENCE LISTING INFORMATION

A computer readable textfile, entitled "DN1K13412.txt (Sequence Listing.txt)" created on or about Sep. 22, 2016, with a file size of about 11 KB, contains the sequence listing for this application and is hereby incorporated by reference in its entirety.

FIELD OF THE DISCLOSURE

The present disclosure describes compositions and methods to promote wound healing. The compositions and methods up-regulate X-box binding protein 1 (XBP1) and/or inositol-requiring enzyme-1 (IRE-1). In various embodiments, the compositions and methods can be used to promote wound healing in diabetic subjects.

BACKGROUND OF THE DISCLOSURE

Protein folding diseases may occur when specific proteins remain unfolded or are misfolded after their synthesis, leaving them unable to perform their particular function. A protein is first made inside the endoplasmic reticulum (ER) of the cytoplasm as a chain of linked amino acids that must be folded in a certain way in order for the protein to be able to perform its specific function. Only correctly folded proteins can be transported to the Golgi apparatus. Unfolded or misfolded proteins can cause harm to the cell due to the loss of the appropriate protein function and also by forming aggregates that can disrupt the protein synthesis and degradation machinery and sequester transcription factors. The exposed hydrophobic amino acids in the unfolded or misfolded forms drive both protein aggregation and binding to certain heat shock proteins (HSPs).

Accumulation of unfolded proteins in a cell leads to ER stress (ERS) in the cell and initiates the unfolded protein response (UPR). The UPR protects cells from the toxic effects of accumulation of unfolded proteins by slowing down protein synthesis, increasing transcription of ER chaperones that bind to unfolded/misfolded proteins and guide their appropriate folding, and by increasing transcription of genes that promote ER associated degradation (ERAD). ERAD is a process that uses HSPs to unfold and properly refold misfolded proteins and also sends the unfolded proteins back to the cytosol for immediate degradation in the proteasome. If these functions are not successful in preventing serious injury to the cell caused by the accumulation of unfolded/misfolded proteins, then UPR initiates cell death through apoptosis pathways in order to eliminate the diseased cells and ensure survival of the organism.

SUMMARY OF THE DISCLOSURE

The current disclosure provides that activation of the unfolded protein response (UPR) by up-regulation of the UPR transducer protein, X-box binding protein 1 (XBP1) and/or inositol-requiring enzyme-1 (IRE-1), promotes wound healing. Wound healing can be promoted in, for example, diabetic subjects.

Two percent of the general population in the United States (U.S.) has slow or non-healing wounds (i.e., chronic wounds). Chronic wounds allow longer time for the development of infections and can contribute to the formation of bed sores and ulcers.

A common comorbid condition with chronic wounds is diabetes mellitus (diabetes). One of the most debilitating complications of chronic wounds in diabetics is the development of chronic foot ulcers. Chronic foot ulcers can necessitate limb amputation, with 50,000-60,000 performed on diabetic patients in the U.S. each year.

Another area where chronic wounds in diabetics create an acute problem is in nursing homes where diabetics are at higher risk of getting bed sores and pressure ulcers. It is estimated that 60,000 patients die each year as a direct result of a pressure ulcer.

By promoting wound healing, the methods of the current disclosure can reduce the occurrence of chronic wounds, thus alleviating these problems, among others.

BRIEF DESCRIPTION OF THE FIGURES

FIG. 11 provides exemplary reference sequences supporting the teachings of the current disclosure.

DETAILED DESCRIPTION

Figure 1:
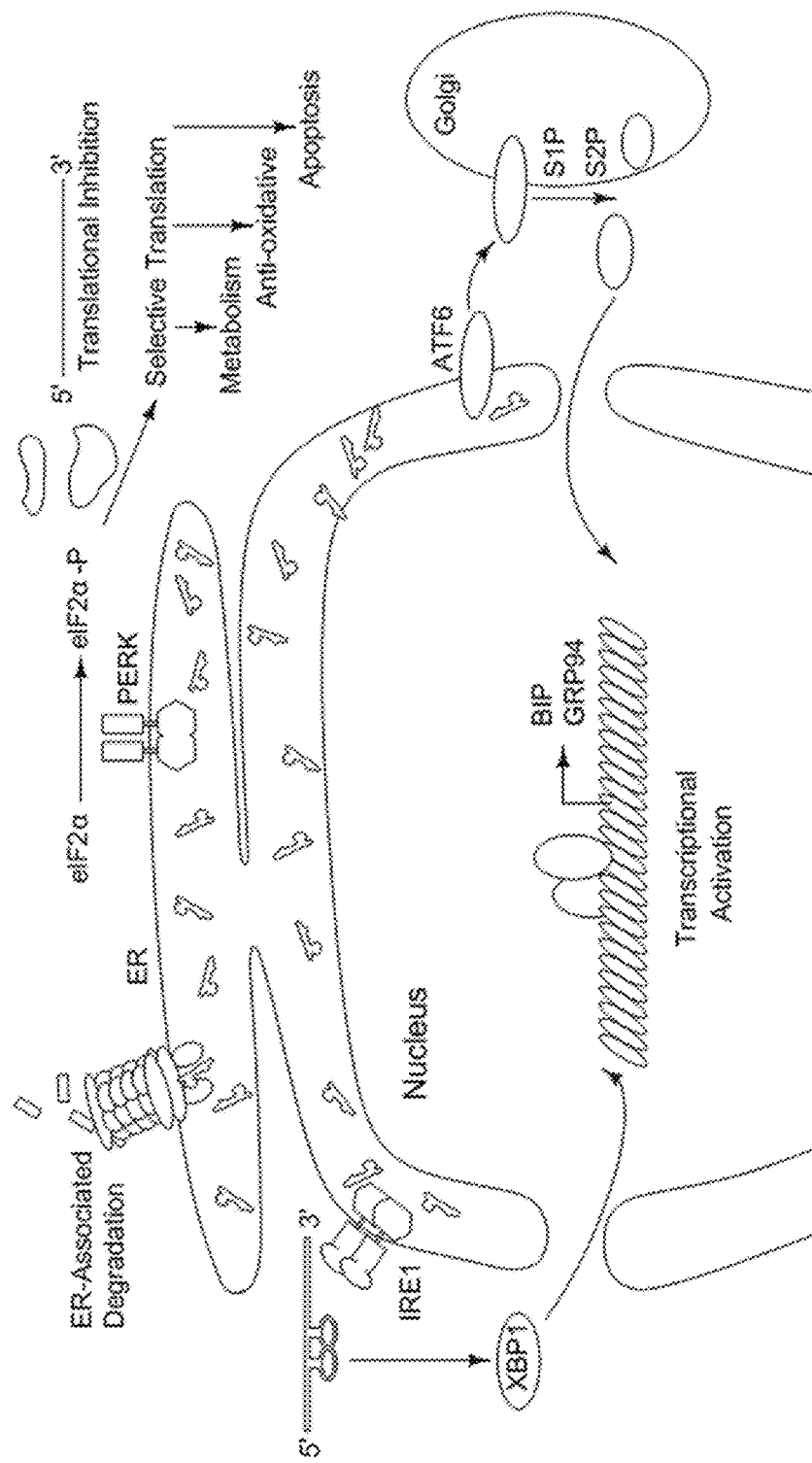
FIG. 1 provides a schematic diagram of the unfolded protein response (UPR).
Figure 2:
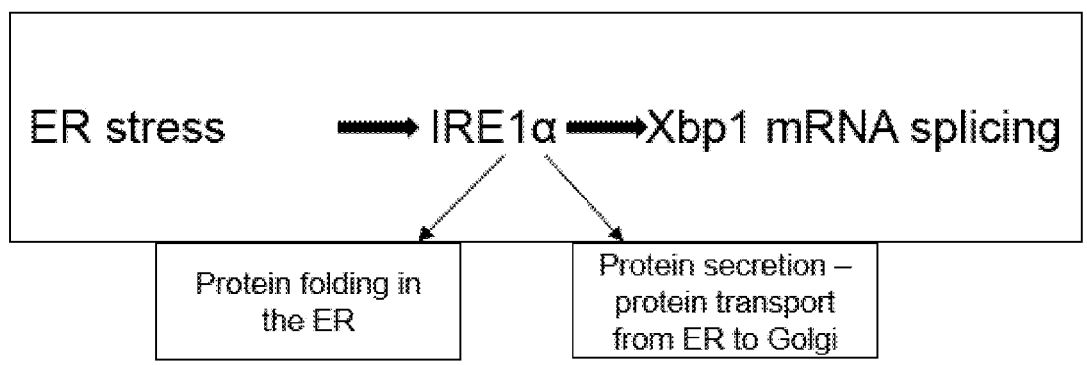
FIG. 2 provides a schematic diagram of the UPR through the IRE-1α/XBP1 pathway.
Figure 3:
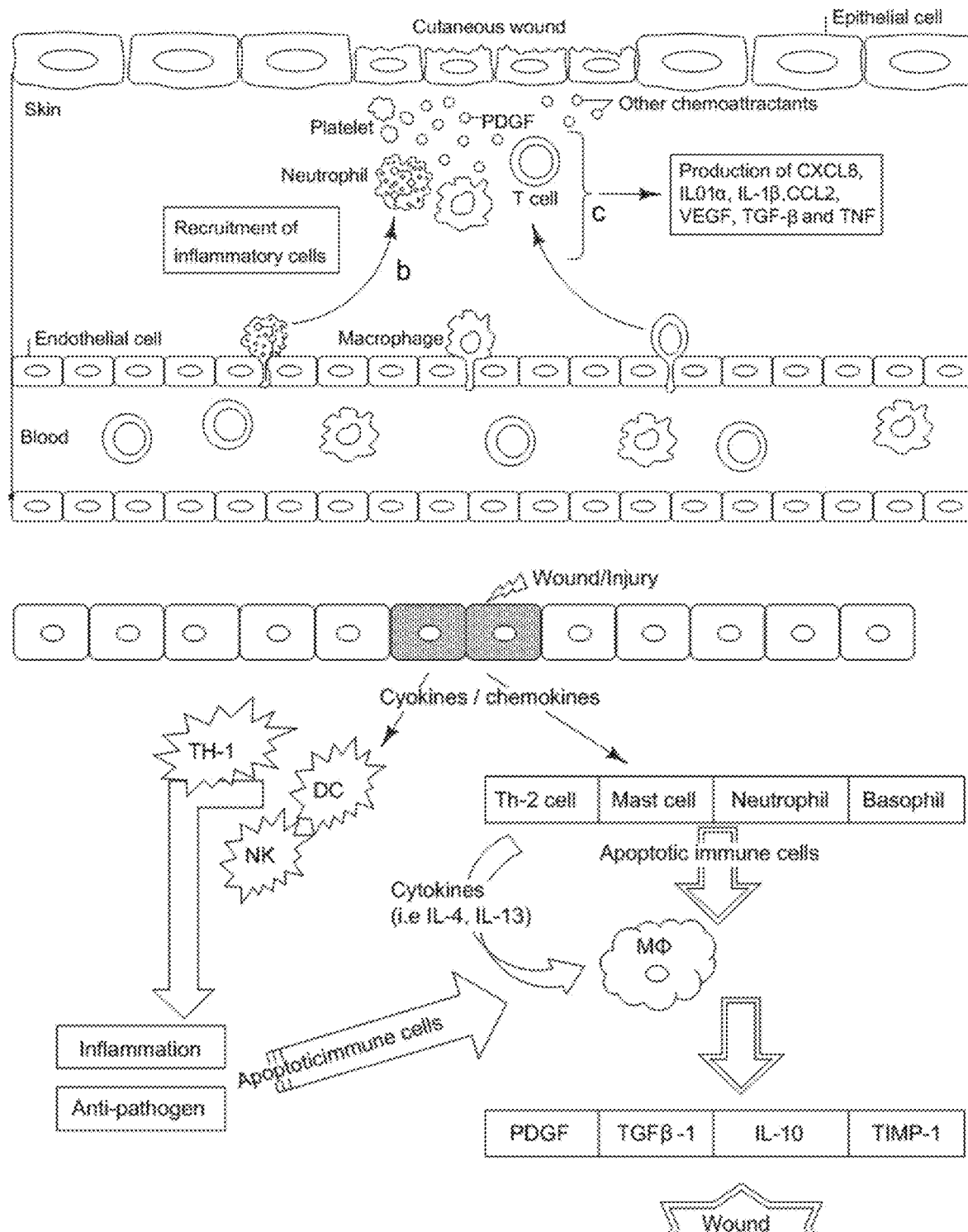
FIG. 3 provides a schematic diagram of skin wound healing processes.
Figure 4:
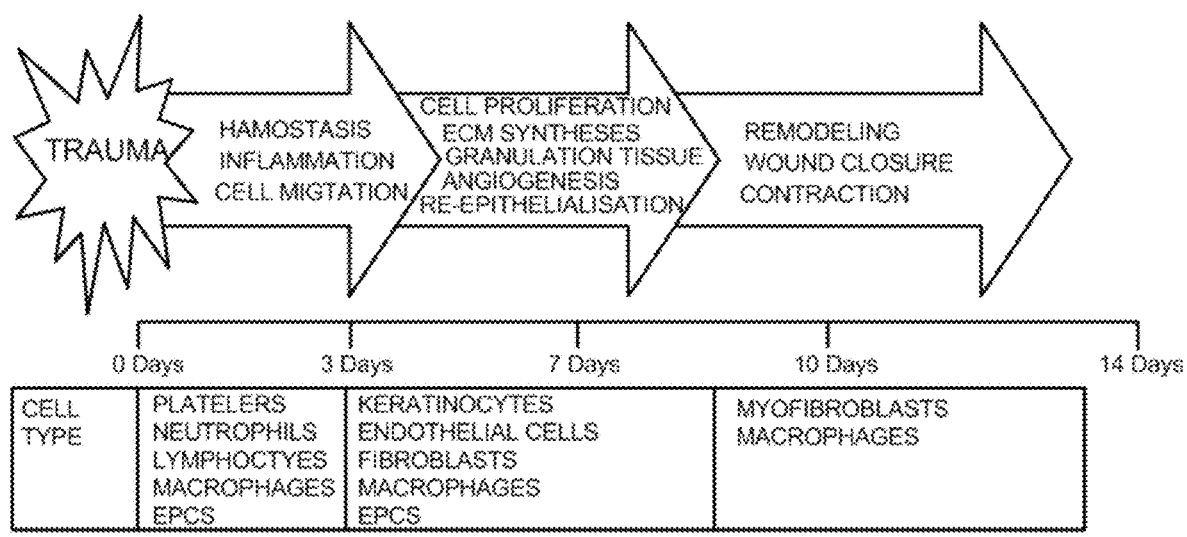
FIG. 4 provides a step-by-step description of physiological processes during wound healing.
Figure 5:
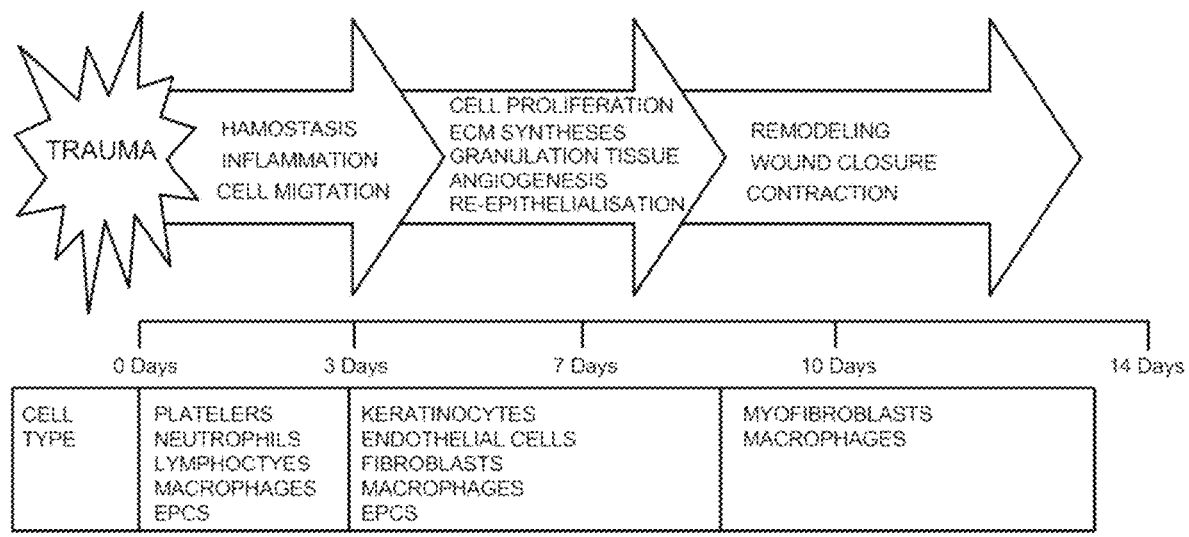
FIG. 5 provides a timeline of the stages of normal cutaneous wound healing.
Figure 6:
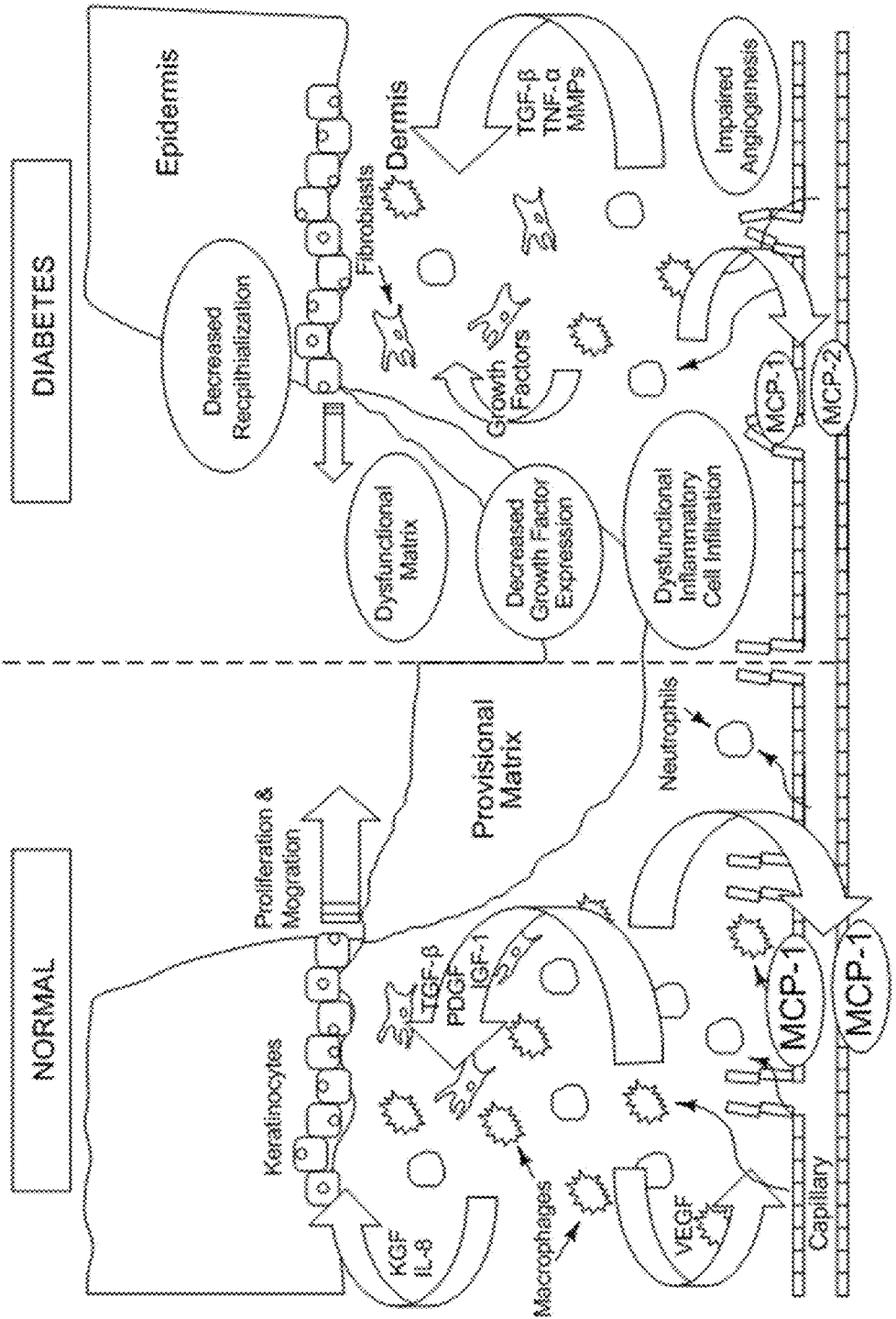
FIG. 6 provides a schematic diagram of normal vs. diabetic healing processes.

Protein folding diseases may occur when specific proteins remain unfolded or are misfolded after their synthesis, leaving them unable to perform their particular function. A protein is first made inside the endoplasmic reticulum (ER) of the cytoplasm as a chain of linked amino acids that must be folded in a certain way in order for the protein to be able to perform its specific function. Only correctly folded proteins can be transported to the Golgi apparatus. Unfolded or misfolded proteins can cause harm to the cell due to the loss of the appropriate protein function and also by forming aggregates that can disrupt the protein synthesis and degradation machinery and sequester transcription factors. The exposed hydrophobic amino acids in the unfolded or misfolded forms drive both protein aggregation and binding to certain heat shock proteins (HSPs).

Accumulation of unfolded proteins in a cell leads to ER stress (ERS) in the cell and initiates the unfolded protein response (UPR). The UPR protects cells from the toxic effects of accumulation of unfolded proteins by slowing down protein synthesis, increasing transcription of ER chaperones that bind to unfolded/misfolded proteins and guide their appropriate folding, and by increasing transcription of genes that promote ER associated degradation (ERAD). ERAD is a process that uses HSPs to unfold and properly refold misfolded proteins and also sends the unfolded proteins back to the cytosol for immediate degradation in the proteasome. If these functions are not successful in preventing serious injury to the cell caused by the accumulation of unfolded/misfolded proteins, then UPR initiates cell death through apoptosis pathways in order to eliminate the diseased cells and ensure survival of the organism.

The current disclosure provides that activation of the unfolded protein response (UPR) by up-regulation of the UPR transducer protein, X-box binding protein 1 (XBP1) and/or inositol-requiring enzyme-1 (IRE-1), promotes wound healing, for example, in diabetic subjects, in subjects with burn wounds, and subjects with pressure wounds.

Two percent of the general population in the United States (U.S.) has slow or non-healing wounds (i.e., chronic wounds). Chronic wounds allow longer time for the development of infections and can contribute to the formation of bed sores and ulcers.

A common comorbid condition with chronic wounds is diabetes mellitus (diabetes). One of the most debilitating complications of chronic wounds in diabetics is the development of chronic foot ulcers. Chronic foot ulcers can necessitate limb amputation, with 50,000-60,000 performed on diabetic patients in the U.S. each year.

Another area where chronic wounds in diabetics create an acute problem is in nursing homes where diabetics are at higher risk of getting bed sores and pressure ulcers. It is estimated that 60,000 patients die each year as a direct result of a pressure ulcer.

The present disclosure describes compositions and methods to promote wound healing. In particular embodiments, the compositions and methods can be used to reduce the occurrence of chronic wounds. In particular embodiments, the compositions and methods can be used to promote wound healing in diabetic subjects. In particular embodiments, the compositions and methods can be used to reduce the occurrence of chronic wounds in diabetic subjects.

Wound healing generally can be divided into three steps: re-epithelialization, granulation, and neovascularization. Delayed re-epithelialization and inadequate formation of granulation tissue can lead to the development of chronic wounds. Endothelial progenitor cells (EPCs), which derive from bone marrow, normally travel to sites of injury and are essential for the formation of blood vessels and wound healing. Without being bound by theory, it is believed in diabetic patients that EPCs are not properly recruited to wound sites so healing is significantly impaired.

A "wound" refers to open wounds, such as incisions, lacerations, abrasions, avulsions, puncture wounds, penetration wounds, gunshot wounds, burn wounds, thermal burns, chemical burns, electrical burns, and radiation burns. Wounds also include pressure wounds. "Chronic wounds" include wounds that take longer to heal than would be expected by a physician. In diabetics, "chronic wounds" include wounds that take longer to heal as compared to a wound of a healthy control subject. For example, a corneal incision wound is expected to heal within 42 hours following its occurrence. In human subjects, a skin laceration is similarly expected to knit closed within 48 hours (if significant emergency care is not required), but would be considered chronic if it had not healed within this time frame.

The present disclosure provides that up-regulation of XBP1 promotes wound healing in a subject. XBP1 is a transcription factor. XBP1 causes the increase of Monocyte chemoattractant protein-1 (MCP1, AKA CCL2). It also increases a small cytokine that belongs to the CC chemokine family. CCL2 recruits monocytes, memory T cells, and dendritic cells to the sites of inflammation produced by either tissue injury or infection. XBP1 also stimulates production of Vascular Endothelial Growth Factors (VEGF) and inflammatory cytokines/chemokines (IL6, IL8, IL1 (3). Up-regulation of XBP1 as disclosed herein increases epithelialization and angiogenesis and reduces contracture(s), the apparent tightening of skin around a wound or burn, and scarring.

IRE-1 has ribonuclease activity that cleaves XBP-1, transforming it into an isoform that increases inflammation, angiogenesis, increases epithelial cell division and other beneficial attributes "Up-regulated" or "Up-regulation" means increasing the presence or activity of a protein and/or increasing the expression of its gene. "Its gene" in reference to a particular protein refers to a nucleic acid sequence (used interchangeably with polynucleotide or nucleotide sequence) that encodes the particular protein. This definition also includes various sequence polymorphisms, mutations, and/or sequence variants wherein such alterations do not substantially affect the identity or function of the particular protein. Identity or function is not substantially affected if the encoded protein shares at least 90-99% sequence identity with the particular protein (sequence identity defined elsewhere) or there is no statistically significant difference in activity between the particular protein as measured by binding studies or relevant activity assays.

The presence or activity of a protein can be up-regulated by one or more of: administering the protein as a composition in a form that will enter a cell; increasing the expression of the protein; administering or expressing a more active variant of the protein, reducing degradation of the protein following expression, etc. To cause an up-regulation through increased expression of a protein, the copy number of its gene or genes encoding the protein may be increased. Alternatively, a strong and/or inducible promoter may be used to direct the expression of the gene, the gene being expressed either as a transient expression vehicle, or homologously or heterologously incorporated into a genome. In another embodiment, the promoter, regulatory region, and/or the ribosome binding site upstream of the gene can be altered to achieve over-expression. The expression may also be enhanced by increasing the relative half-life of the messenger or other forms of RNA. Similar mechanisms can be used to up-regulate the expression of genes, for example, genes encoding XBP1 or IRE-1.

As is understood by one of ordinary skill in the art, "up-regulation" can be measured against a relevant control condition. For example, an up-regulation of XBP1 can be measured by comparing an XBP1 level to that observed in a wound area of a diabetic subject that has not received a treatment disclosed herein. An up-regulation of XBP1 can also be evidenced by an increase in angiogenesis, growth factor production, macrophage function, and/or endothelial matrix formation at a site of interest, such as a healing wound.

Variants of proteins disclosed herein can also be administered (e.g., controllably expressed). "Variants" include proteins having one or more amino acid additions, deletions, stop positions, or substitutions, as compared to a reference protein disclosed herein. SEQ ID NO: 1 represents the amino acid sequence of human XBP1 and is a reference sequence for purposes of the present disclosure. SEQ ID NO: 2 represents the amino acid sequence of IRE-1 and is a reference sequence for purposes of the present disclosure. These reference sequences are provided in FIG. 11.

An amino acid substitution can be a conservative or a non-conservative substitution. Variants of proteins disclosed herein can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other groups including amino acids that are considered conservative substitutions for one another include: sulfur-containing: Met and Cys; acidic: Asp, Glu, Asn, and Gin; small aliphatic, nonpolar or slightly polar residues: Ala, Ser, Thr, Pro, and Gly; polar, negatively charged residues and their amides: Asp, Asn, Glu, and Gin; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W. H. Freeman and Company.

Variants of proteins disclosed herein also include proteins with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a protein sequence disclosed herein.

Variants of therapeutic proteins disclosed herein include proteins that share: 70% sequence identity with SEQ ID NO:1 or 2; 75% sequence identity with any of SEQ ID NO: 1 or 2; 80% sequence identity with any of SEQ ID NO: 1 or 2; 81% sequence identity with any of SEQ ID NO: 1 or 2; 82% sequence identity with any of SEQ ID NO: 1 or 2; 83% sequence identity with any of SEQ ID NO: 1 or 2; 84% sequence identity with any of SEQ ID NO: 1 or 2; 85% sequence identity with any of SEQ ID NO: 1 or 2; 86% sequence identity with any of SEQ ID NO: 1 or 2; 87% sequence identity with any of SEQ ID NO: 1 or 2; 88% sequence identity with any of SEQ ID NO: 1 or 2; 89% sequence identity with any of SEQ ID NO: 1 or 2; 90% sequence identity with any of SEQ ID NO: 1 or 2; 91% sequence identity with any of SEQ ID NO: 1 or 2; 92% sequence identity with any of SEQ ID NO: 1 or 2; 93% sequence identity with any of SEQ ID NO: 1 or 2; 94% sequence identity with any of SEQ ID NO: 1 or 2; 95% sequence identity with any of SEQ ID NO: 1 or 2; 96% sequence identity with any of SEQ ID NO: 1 or 2; 97% sequence identity with any of SEQ ID NO: 1 or 2; 98% sequence identity with any of SEQ ID NO: 1 or 2; or 99% sequence identity with any of SEQ ID NO: 1 or 2.

"% sequence identity" refers to a relationship between two or more sequences, as determined by comparing the sequences. In the art, "identity" also means the degree of sequence relatedness between protein or nucleotide sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisc.); BLASTP, BLASTN, BLASTX (Altschul, et al., J. Mol. Biol. 215:403-410 (1990); DNASTAR (DNASTAR, Inc., Madison, Wisc.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" mean any set of values or parameters which originally load with the software when first initialized.

Nucleotide sequences encoding the disclosed proteins can be readily deduced by one of ordinary skill in the art.

Prior publications have shown a correlation of some UPR markers and chronic inflammation with diabetic wound conditions. It should be clarified that, as a protective and defensive response, UPR is activated upon stress, injuries, or pathological conditions. The primary role of UPR is to provide survival signals by helping cells or tissues overcome or adapt to stress conditions. However, when stress gets prolonged, chronic UPR or inflammation may contribute to pathological conditions. However, this "side effect" of persistent activation of UPR or inflammation should not subside the primary roles of UPR or inflammation as protective, beneficial responses to injuries or other forms of stress.

Schürmann et al., Biochem. And Biophys. Res. Comm. (2014) 446 (1), 195-200 described the association of some UPR components, including XBP1, with diabetic wound conditions. However, they did not study any functional involvement of XBP1 in diabetic wound healing processes. Cultured cells were utilized to explore the connection of ER stress response and chronic inflammation. The in vitro-cultured transformed cell line cannot recapitulate in vivo diabetic wound models.

Other groups (Barbhaiya et al., (2012) J. of the Amer. College of Surgeons, 215(3), S85) have advocated inhibiting XBP1 to inhibit the ER stress response to prevent excessive keloid or scar formation, a condition usually seen in individuals with scar diathesis. The conception of this group's study was that inhibiting the ER stress response would help to heal wounds with excessive keloid or scar formation. In other words, they proposed that inhibitors of the ER stress response could be used to treat wounds that heal too robustly, in order to prevent, for example, keloid formation or excessive scar formation.

Conversely, the disclosed strategy, based on confirmed evidence in animal studies, shows that activating transient and controlled ER stress response promotes healing processes in wounds such as diabetic wounds, in which re-epithelialization and scar formation are usually deficient or delayed. Due to the improved re-epithelialization and reduced contracture(s) in the animal wounds that receive XBP1 up-regulation treatment, this approach should also succeed in burn wounds and pressure wounds. Thus, the current disclosure addresses a different scenario related to wound healing and more particularly, diabetic wound healing. The current disclosure utilizes the protective, beneficial aspects of URP for skin wound healing in a manner wherein the activation of UPR and/or up-regulation (e.g., expression) of XBP1 or IRE-1 is transient and controlled.

In particular embodiments, XBP1 is up-regulated by administering a vector including a nucleotide sequence that encodes for and directs expression of XBP1 and/or IRE-1. The nucleotide sequence can also direct expression of an XBP1 and/or IRE-1 prodrug or a protein or other molecule that stimulates a cell to produce or activate XBP1 (e.g., IRE-1).

Prodrugs refer to a protein that can undergo biotransformation (e.g., either spontaneous or enzymatic) within a subject to release, or to convert to, (e.g., enzymatically, mechanically, electromagnetically, etc.) an active or more active form of the expressed protein. Prodrugs can be used to overcome issues associated with stability, toxicity, lack of specificity, or limited bioavailability. Some preferred prodrugs are variants of proteins that have sequences that are cleavable under metabolic conditions. Exemplary prodrugs become active or more active in vivo when they undergo a biochemical transformation (e.g., phosphorylation, hydrogenation, dehydrogenation, glycosylation, etc.). See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, Calif. (1992)).

Vectors or other administration forms (e.g., therapeutic proteins) can be incorporated into compositions for administration to subject. Compositions include an administration form (e.g. vector, nanoparticle) and at least one pharmaceutically acceptable excipient. Delivery to a subject can be in accordance with any known methods of drug delivery.

The described compositions can deliver relevant therapeutics directly or can administer genetic therapies to up-regulate XPB1 and/or IRE-1. A desired gene can be introduced intracellularly and incorporated within subject cellular DNA for expression, by homologous recombination (Koller and Smithies, 1989, Proc. Natl. Acad. Sci. USA 86:8932-8935; Zijlstra et al., 1989, Nature 342:435-438).

In particular embodiments, the vector is selected from a DNA vector, a RNA vector, a viral vector, a bacterial vector, a plasmid vector, a cosmid vector, an artificial chromosome vector, such as a yeast artificial chromosome vector.

Viral vectors are usually non-replicating or replication-impaired vectors, which means that the viral vector cannot replicate to any significant extent in normal cells (e.g., normal human cells), as measured by conventional means (e.g. via measuring DNA synthesis and/or viral titer). Non-replicating or replication-impaired vectors may have become so naturally (i.e., they have been isolated as such from nature) or artificially (e.g., by breeding in vitro or by genetic manipulation). There will generally be at least one cell-type in which the replication-impaired viral vector can be grown—for example, modified vaccinia Ankara (MVA) can be grown in CEF cells. Typically, viral vectors are incapable of causing a significant infection in a subject, typically in a mammalian subject.

In particular embodiments, the vector is selected from an adenovirus or a poxvirus vector. Examples of viral vectors that are useful in this context include attenuated vaccinia virus vectors such as modified vaccinia Ankara (MVA) and NYVAC, or strains derived therefrom. Other examples of vectors include an avipox vector, such as a fowlpox vectors (e.g., FP9) or canarypox vectors (e.g., ALVAC and strains derived therefrom). Alternative viral vectors include adeno-viral vectors (e.g., non-human adenovirus vectors), alphavirus vectors, flavivirus vectors, herpes viral vectors (e.g., herpes simplex, CMV and EBV), influenza virus vectors and retroviral vectors.

In particular embodiments, the vector is a human adenovirus. In another embodiment, the vector is a simian adenovirus. In another embodiment, the vector is a chimpanzee adenovirus. A chimpanzee as referred to herein may include Pan troglodytes (common chimpanzee) and Pan paniscus (Bonobo). In particular embodiments, the vector is selected from adenovirus 5 (Ad5), adenovirus 35 (Ad35), adenovirus 11 (Ad11), adenovirus 26 (Ad26), adenovirus 48 (Ad48) or adenovirus 50 (Ad50).

Additional information about retroviral vectors can be found in, for example, Miller et al., 1993, Meth. Enzymol. 217:581-599; Boesen et al., 1994, Biotherapy 6:291-302, Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114; additional information about adenoviruses can be found in, for example, Kozarsky and Wilson, 1993, Current Opinion in Genetics and Development 3:499-503, Rosenfeld et al., 1991, Science 252:431-434; Rosenfeld et al., 1992, Cell 68:143-155; and Mastrangeli et al., 1993, J. Clin. Invest. 91:225-234; additional information about adena-associated viruses, mammalian artificial chromosomes can be found in, for example, Vos, 1998, Curr. Op. Genet. Dev. 8:351-359; additional information about triplex DNA can be found in, for example, Chan and Glazer, 1997, J. Mol. Med. 75:267-282; and additional information about ribozymes can be found in, for example, Branch and Klotman, 1998, Exp. Nephrol. 6:78-83.

Expression of vectors may be controlled following administration to a subject. In particular embodiments, the desired gene recombinantly expressed in the subject includes an inducible promoter operably linked to the coding region, such that expression of the recombinant gene is controllable by controlling the presence or absence of the appropriate inducer of transcription.

For example, a number of cell- or tissue-specific promoters are known. To accommodate required flexibility in disparate levels and timing of expression such genes are driven from low basal promoters (i.e. TK), or through controlled induction from a Tet on/off promoter. The Tet promoter system benefits from the use of innocuous antibiotic analogs such as anhydrotetracycline, which activates the Tet promoter at concentrations 2 logs lower than with tetracycline, does not result in dysregulation of intestinal flora, does not result in resistance to polyketide antibiotics, and does not exhibit antibiotic activity. Anhydrotetracycline is fully soluble in water, and can be administered in drinking rations to potentiate activation of selected genes in transfected cells. The potential toxicity of anhydrotetracycline, the first breakdown product of tetracycline in the human body, can be circumvented by administration of other analogs, such doxycycline, an FDA-approved tetracycline analog that also activates the Tet on/off promoter system. This system can be employed in the design of a failsafe "kill switch" by tightly regulating inducible expression of a potent pro-apoptotic gene (e.g. Bax) to initiate targeted apoptosis of transfected cells in the event of untoward side effects or when the desired therapeutic endpoint has been achieved. Recent advances in the Tet-on system have resulted in much enhanced repression of promoter leakiness and responsiveness to Dox at concentrations up to 100-fold lower than in the original Tet system (Tet-On Advanced™ Tet-On 3G™). For additional information on TET systems, see, for example, Bujard & Gossen (1992). Proc. Natl. Acad. Sci. U.S.A. 89 (12): 5547-51; Urlinger et al., (2000). Proc. Natl. Acad. Sci. U.S.A. 97 (14): 7963-8; and Zhou et al., (2006). Gene Ther. 13 (19): 1382-1390.

The GAL4-UAS system may also be used. For additional information on GAL4-UAS systems, see, for example, Brand & Perrimon (Jun. 1, 1993). Development 118: 401-415; Duffy (2002). Genesis 32: 1-15; Janice et al., (1988). Nature (6167): 853-6; Webster et al., (1988). Cell 52 (2): 169-78; Liu & Lehman (2008). Proc Natl Acad Sci UAS 99 (3): 1377-82; Davison et al., (2007). Developmental Biology 304 (2): 811-24; Suster, et al., (2004). Genesis (Wiley Online Library) 39 (4): 240-245; and Luan et al., (2006). Neuron (Elsevier) 52 (3): 425-436.

In particular embodiments, vectors used within the current disclosure do not stimulate vector-derived immunity that would prevent a subsequent use of the disclosed treatments in a subject. This benefit can be confirmed by designing a sensitive assay to detect immune responses (antibody ELISA and T-cell based assays) to components of the treatment.

Particular embodiments utilize adeno-associated virus (AAV). AVV is a small virus which infects humans and some other primate species. AAV is not currently known to cause disease. The virus causes a very mild immune response, lending further support to its apparent lack of pathogenicity. Gene therapy vectors using AAV can infect both dividing and quiescent cells and persist in an extrachromosomal state without integrating into the genome of the host cell. The AVV system also utilizes the Tet-On/Off system as an additional precaution.

Figure 10:
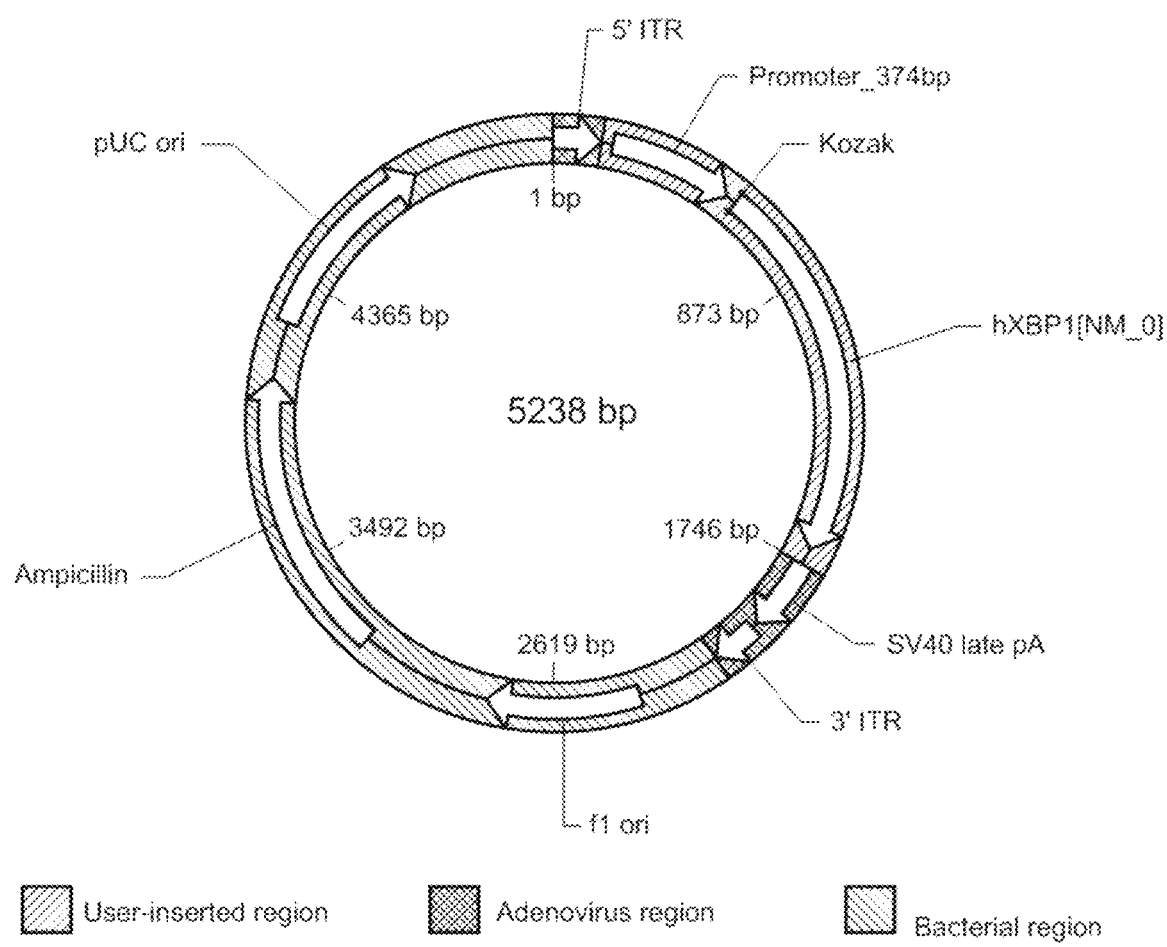
FIG. 10 provides a schematic diagram for an appropriate vector and Tet On/Off mechanism for use in the methods disclosed herein.
Figure 10:
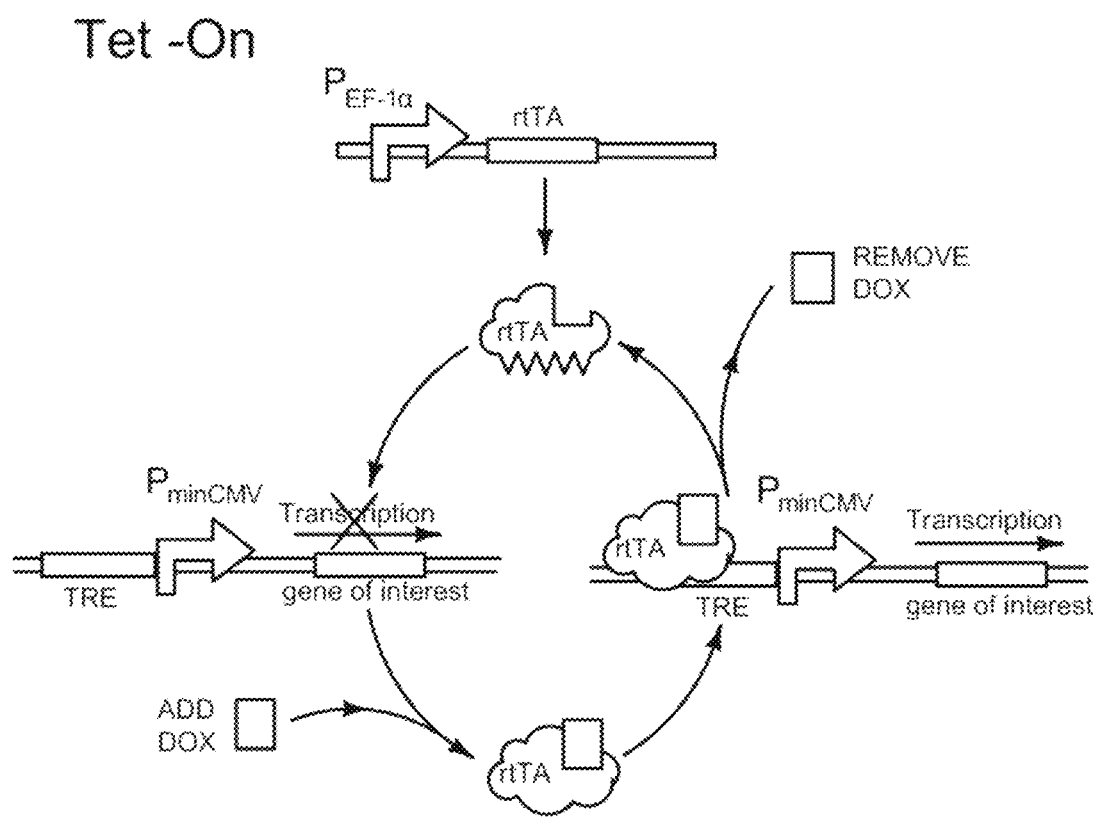

Exemplary vectors were obtained from VectorBuilder:
Vector Name: pAAV-tet_on_promoter-hXBP1
Size 5238 bp
Vector Type Adeno-associated viral gene expression vector
Inserted Promoter: 3rd generation high-specific, high-efficiency Tet-On promoter_374 bp
Inserted ORF: Human activated form of XBP1 cDNA (hXBP1).
GeneBank ID: NM 001079539.1
Control AAV vector: pAAV-tet_on_promoter-Luciferase
Size 5760 bp
Vector Type Adeno-associated viral gene expression vector
Inserted Promoter: 3rd generation high-specific, high-efficiency Tet-On promoter_374 bp
Inserted ORF: Luciferase reporter cDNA.
GeneBank ID: AAA89082
See, for example, FIG. 10.

Administration methods can also include nanoparticle gene transfer technology to deliver Tet On-controlled XBP1 and/or IRE-1 cDNA into wounded skin cells.

Administration methods can also include impalefection technology to deliver XBP1 and/or IRE-1 expression DNA vector to wounded skin cells. Impalefection is a method of gene delivery using nanomaterials, such as carbon nanofibers, carbon nanotubes, and nanowires. One of the features of impalefection is spatially resolved gene delivery that holds potential for tissue engineering approaches in wound healing as gene activated matrix technology (J Regener Med 2000, 1: 25-29).

Administration methods can also include cell therapy or engineered skin layer technology. The AAV-XBP1 and/or IRE-1 can be transfected into epithelial cells or ex vivo cultured skin layer that can be applied to skin wounds. By utilizing the teachings of the disclosure, epithelial cells or engineered skin tissues with controlled expression of XBP1 and/or IRE-1 represent a very promising therapeutic approach for skin wound healing.

Purified human XBP1 and/or IRE-1 protein also can be delivered into wound skin cells through gold nanoparticle-mediated laser transfection (Laser-Gold Nanoparticle Technology: Nanotechnology 2014, 25:245101).

Additional information about liposomes can be found in, for example, Tarahovsky and Ivanitsky, 1998, Biochemistry (Mose) 63:607-618.

Genetic therapies can be achieved using any method known in the art, including transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, sheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present disclosure.

In some embodiments, the pharmaceutical compositions can include, for example, 25 µg/mL-5 mg/mL, 50 µg/mL-5 mg/mL, 100 µg/mL-5 mg/mL, 150 µg/mL-5 mg/mL, 200 µg/mL-5 mg/mL, 250 µg/mL-5 mg/mL, 300 µg/mL-5 mg/mL, 350 µg/mL-5 mg/mL, 400 µg/mL-5 mg/mL, 450 µg/mL-5 mg/mL, 500 µg/mL-5 mg/mL, 550 µg/mL-5 mg/mL, 600 µg/mL-5 mg/mL, 650 µg/mL-5 mg/mL, 700 µg/mL-5 mg/mL, 750 µg/mL-5 mg/mL, 800 µg/mL-5 mg/mL, 850 µg/mL-5 mg/mL, 900 µg/mL-5 mg/mL, 950 µg/mL-5 mg/mL, 1 mg/mL-5 mg/mL, 1.5 mg/mL-5 mg/mL, 2 mg/mL-5 mg/mL, 2.5 mg/mL-5 mg/mL, 3 mg/mL-5 mg/mL, 3.5 mg/mL-5 mg/mL, 4 mg/mL-5 mg/mL, 4.5 mg/mL-5 mg/mL, 25 µg/mL-2.5 mg/mL, 50 µg/mL-2.5 mg/mL, 100 µg/mL-2.5 mg/mL, 150 µg/mL-2.5 mg/mL, 200 µg/mL-2.5 mg/mL, 250 µg/mL-2.5 mg/mL, 300 µg/mL-2.5 mg/mL, 350 µg/mL-2.5 mg/mL, 400 µg/mL-2.5 mg/mL, 450 µg/mL-2.5 mg/mL, 500 µg/mL-2.5 mg/mL, 550 µg/mL-2.5 mg/mL, 600 µg/mL-2.5 mg/mL, 650 µg/mL-2.5 mg/mL, 700 µg/mL-2.5 mg/mL, 750 µg/mL-2.5 mg/mL, 800 µg/mL-2.5 mg/mL, 850 µg/mL-2.5 mg/mL, 900 µg/mL-2.5 mg/mL, 950 µg/mL-2.5 mg/mL, 1 mg/mL-2.5 mg/mL, 1.5 mg/mL-2.5 mg/mL, 2 mg/mL-2.5 mg/mL, 25 µg/mL-1 mg/mL, 50 µg/mL-1 mg/mL, 100 µg/mL-1 mg/mL, 150 µg/mL-1 mg/mL, 200 µg/mL-1 mg/mL, 250 µg/mL-1 mg/mL, 300 µg/mL-1 mg/mL, 350 µg/mL-1 mg/mL, 400 µg/mL-1 mg/mL, 450 µg/mL-1 mg/mL, 500 µg/mL-1 mg/mL, 550 µg/mL-1 mg/mL, 600 µg/mL-1 mg/mL, 650 µg/mL-1 mg/mL, 700 µg/mL-1 mg/mL, 750 µg/mL-1 mg/mL, 800 µg/mL-1 mg/mL, 850 µg/mL-1 mg/mL, 900 µg/mL-1 mg/mL, 950 µg/mL-1 mg/mL, 25 µg/mL-750 µg/mL, 50 µg/mL-750 µg/mL, 100 µg/mL-750 µg/mL, 150 µg/mL-750 µg/mL, 200 µg/mL-750 µg/mL, 250 µg/mL-750 µg/mL, 300 µg/mL-750 µg/mL, 350 µg/mL-750 µg/mL, 400 µg/mL-750 µg/mL, 450 µg/mL-750 µg/mL, 500 µg/mL-750 µg/mL, 550 µg/mL-750 µg/mL, 600 µg/mL-750 µg/mL, 650 µg/mL-750 µg/mL, 700 µg/mL-750 µg/mL, 25 µg/mL-500 µg/mL, 50 µg/mL-500 µg/mL, 100 µg/mL-500 µg/mL, 150 µg/mL-500 µg/mL, 200 µg/mL-500 µg/mL, 250 µg/mL-500 µg/mL, 300 µg/mL-500 µg/mL, 350 µg/mL-500 µg/mL, 400 µg/mL-500 µg/mL, 450 µg/mL-500 µg/mL, 25 µg/mL-250 µg/mL, 50 µg/mL-250 µg/mL, 100 µg/mL-250 µg/mL, 150 µg/mL-250 µg/mL, 200 µg/mL-250 µg/mL, 25 µg/mL-100 µg/mL, or 50 µg/mL-100 µg/mL of the administration form.

In particular embodiments, the compositions disclosed herein can be formulated for topical administration. The compositions disclosed herein can also be formulated for intradermal, intralesional, intraocular, intravaginal, intrarectal, intramuscular, and/or subcutaneous administration.

In particular embodiments, the compositions can be in the form of, e.g., gels, ointments, pastes, lotions, creams, sprays, foams, or powders.

A gel is a substantially dilute cross-linked system, which exhibits no flow when in the steady-state. Most gels are liquid, however they behave more like solids due to the three-dimensional cross-linked network within the liquid. Gels can have properties ranging from soft and weak to hard and tough.

An ointment is a homogeneous, viscous, semi-solid preparation, most commonly a greasy, thick oil (oil 80%-water 20%) with a high viscosity. Ointments have a water number, which is the maximum quantity of water that 100 g of a base can contain at 20° C.

A paste includes three agents—oil, water, and powder, one of which includes a therapeutic agent. Pastes can be an ointment in which a powder is suspended.

A lotion also includes oil, water, and powder, but can have additional components (e.g., alcohol to hold the emulsion together) and often has a lower viscosity than a paste.

A cream is an emulsion of oil and water in approximately equal proportions. Creams are thicker than lotions and maintain their shape when removed from a container.

Topical formulations disclosed herein can include components, such as animal and vegetable fats, oils, waxes, paraffins, starch, tragacanth, cellulose derivatives, polyethylene glycols, silicones, bentonites, silicic acid, talc and zinc oxide, or mixtures thereof. In various embodiments, topical formulations may include thickening agents, surfactants, organic solvents, tonicity modifiers, In various embodiments, topical formulations can be prepared using thickening agents, such as carboxymethylcellulose sodium, sodium starch glycollate type C, or Carbomers such as Carbopol® (Lubrizol Advanced Materials, Inc. Cleveland, Ohio, USA) 934, 980, 981, 1382, 5984, or 2984. In various embodiments, topical formulations can be prepared using surfactants, such as Pluronic® (BASF Corporation, Mount Olive, N.J., USA) co-polymers, such as Pluronic® F-127, and/or a Pluronic® co-polyer having the formula

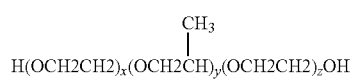

or $H[OCH_2CH_2]_{49}[OCHCH_2]_{67}[OCH_2CH_2]_{49}OH$; propyl glycol, polypropylene glycol (PPG) stearyl ethers, such as PPG ethers of stearyl alcohol including PPG-20 methyl glucose ether distearate, PPG-15 Stearyl Ether, and PPG-11 Stearyl Ether.

In various embodiments, topical formulations such as gel formulations may include an organic solvent (e.g. a lower alkyl alcohol, such as ethyl alcohol or isopropyl alcohol; a ketone, such as acetone or N-methyl pyrrolidone; a glycol, such as propylene glycol; and the like, or mixtures thereof) present in an amount of 1% to 99%. In particular embodiments, an organic solvent may be present in an amount of 60% to 80%. In various embodiments, topical formulations may include a cellulose derivative, such as hydroxyl ethyl cellulose, hydroxy propyl cellulose, hydroxy propyl methyl cellulose, methyl cellulose, carboxy methyl cellulose, sodium carboxy methyl cellulose, ethyl cellulose, and the like, or combinations thereof present in an amount of 0.1% to 20%. In particular embodiments, a cellulose derivative may be present in an amount of 0.5% to 5%.

In various embodiments, topical formulations such as gel formulations include any suitable tonicity modifier. Exemplary suitable tonicity modifiers include sodium chloride, potassium chloride, mannitol, sucrose, lactose, fructose, maltose, dextrose, dextrose anhydrous, propylene glycol, and glycerol. In various embodiments, the tonicity modifier can be present in an amount of 0.5% to 1% by weight. In particular embodiments, a tonicity modifier can be present in an amount of 0.8% to about 1% by weight of the topical formulation. In various embodiments, buffers can be present in the topical formulations. Exemplary buffers include phosphate buffered saline (PBS) acetate buffers, such as sodium acetate trihydrate or glacial acetic acid; and citrate buffers, such as sodium citrate dihydrate and citric acid.

In some embodiments, topical formulations such as gel formulations may have a viscosity of at least 1,000 centipoise (cps). In other embodiments, topical formulations such as gel formulations may have a viscosity of at least about 3,000 cps. In specific embodiments, the viscosity of topical formulations will not exceed 50,000 cps.

Powders and sprays particularly may benefit from the inclusion of excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. The compositions of the disclosure can be alternatively administered by aerosol. This is accomplished by preparing an aqueous aerosol, liposomal preparation, or solid particles containing a composition of the disclosure. A non-aqueous (e.g., fluorocarbon propellant) suspension also could be used. Sonic nebulizers can be preferred because they minimize exposing the compositions to shear, which can result in degradation of the composition.

Compositions can also be incorporated into wound dressings (e.g., bandages, adhesive bandages, transdermal patches). Generally, in these embodiments, compositions are embedded within puffs, gauzes, fleeces, gels, powders, sponges, or other materials that are associated with a second layer to form a wound dressing. Absorption enhancers can also be used to increase the flux of the composition, and particularly the administration form within the composition, across the skin. The rate of such flux can be controlled by either providing a rate controlling membrane or dispersing the administration form in a polymer matrix or gel.

In particular embodiments, the second layer of a wound dressing can be an elastomeric layer, vapor-permeable film, waterproof film, a woven or nonwoven fabric, mesh, or the like. The composition containing layer and second layer can be bonded using any suitable method (e.g., the application of adhesives, such as pressure sensitive adhesives, hot melt adhesives, curable adhesives; the application of heat or pressure, such as in lamination; a physical attachment through the use of stitching, studs, other fasteners; or the like).

Wound dressings may include adhesives for attachment to the skin or other tissue. Although any adhesive suitable for forming a bond with the skin or other tissue can be used, in certain embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability of a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

In particular embodiments, the pressure sensitive adhesive can include a butyl acrylate. While butyl acrylate pressure sensitive adhesives can generally be used for many applications, any pressure sensitive adhesive suitable for bonding skin can be used. Such pressure sensitive adhesives are well known in the art.

In other embodiments, the compositions disclosed herein may be formulated for injection, including subcutaneous, subdermal, and/or intraocular. U.S. Pat. No. 7,918,824 discloses syringes suitable for subject use. The compositions for injection can take such forms as suspensions, solutions or emulsions in oily or aqueous vehicles, and can contain formulatory agents such as suspending, stabilizing, preserving and/or dispersing agents. Injectable formulations include one or more compositions disclosed herein in combination with one or more pharmaceutically acceptable sterile isotonic aqueous or non-aqueous solutions, emulsions, or sterile powders which may be reconstituted into sterile injectable solutions or dispersions just prior to use, which may contain antioxidants, buffers, bacteriostats, or solutes.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the pharmaceutical compositions.

Alternatively, the administration form can be in lyophilized and/or provided in powder form for constitution with a suitable vehicle, e.g., sterile pyrogen-free water, before use. Lyophilized compositions can include less than 5% water content; less than 4.0% water content; or less than 3.5% water content.

In another embodiment, the composition can be in a unit dosage form, such as in a suitable diluent in sterile, hermetically sealed ampoules or sterile syringes.

In some cases, in order to prolong the effect of a composition, it is desirable to slow the absorption of the composition following injection. Compositions can be formulated as sustained-release systems utilizing semipermeable matrices of solid polymers containing at least one administration form. Various sustained-release materials have been established and are well known by those of ordinary skill in the art. Sustained-release systems may, depending on their chemical nature, release active ingredients following administration for a few weeks up to over 100 days.

In various embodiments, delayed absorption can be accomplished by dissolving or suspending the composition in an oil vehicle. In various embodiments, administration forms can be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. In addition, prolonged absorption of the injectable pharmaceutical form may be brought about by the inclusion of agents which delay absorption such as aluminum monostearate and gelatin.

Injectable depot forms can be made by forming microencapsule matrices of administration forms in biodegradable polymers such as polylactide-polyglycolide. Depending on the ratio of administration form to polymer, and the nature of the particular polymer employed, the rate of administration form release can be controlled. Examples of other biodegradable polymers include poly(orthoesters) and poly(anhydrides). Injectable depot formulations are also prepared by entrapping the administration form in liposomes or microemulsions which are compatible with body tissue.

Alternatively, delayed absorption of a composition can be accomplished by the use of a liquid suspension of crystalline or amorphous material having poor water solubility. The rate of absorption of the composition then depends upon its rate of dissolution which, in turn, may depend upon crystal size and crystalline form.

Any composition disclosed herein can advantageously include any other pharmaceutically acceptable carriers which include those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with administration forms disclosed herein including salts and prodrugs thereof. Treating subjects includes delivering therapeutically effective amounts. Therapeutically effective amounts include those that provide effective amounts, prophylactic treatments, and/or therapeutic treatments. Therapeutically effective amounts can be administered to promote wound healing. In particular embodiments, the promotion of wound healing leads to re-epithelialization, and reduction in the occurrence and/or severity of chronic wounds such as ulcers.

An "effective amount" is the amount of a therapeutic protein necessary to result in a desired physiological change in the subject. Effective amounts are often administered for research purposes. Effective amounts disclosed herein promote wound healing.

A "prophylactic treatment" includes a treatment administered to a subject who displays signs or symptoms of wounds that have not yet become chronic or display only early signs or warning symptoms for the development of chronic wounds such that treatment is administered for the purpose of diminishing, preventing, or decreasing the risk of the wound becoming chronic or developing the chronic wounds further. Thus, a prophylactic treatment functions as a preventative treatment against chronic wounds. A prophylactic treatment also can be administered to subjects at risk for developing chronic wounds before early signs or warning appear. For example, in subjects at risk for developing chronic wounds, prophylactic treatments can be administered at the time a wound occurs or as soon as is reasonably or practically possible thereafter. Diabetic subjects are one group of subjects at risk for developing chronic wounds. Other subjects at risk for developing chronic wounds include those who suffer from an inflammatory condition.

A "therapeutic treatment" includes a treatment administered to a subject who has chronic wounds and is administered to the subject for the purpose of promoting the healing of the chronic wounds. Therapeutic treatments can promote wound healing.

Objective measures for the promotion of wound healing include the time required for the closure of an open wound or establishment of a biological barrier, or according to the methods described in Example 1. For example, diabetic subjects provided with a treatment disclosed herein will demonstrate faster wound healing than diabetic subjects with a similar wound who do not receive a treatment disclosed herein.

Objective measures for re-epithelialization can include slit lamp microscopy with fluorescence staining. Objective measures for reduction and/or severity of ulcers can include slit lamp microscopy for surface (ir)regularity.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by a physician, veterinarian, or researcher taking into account parameters such as physical and physiological factors including target, body weight, severity of wound, type of wound, previous or concurrent therapeutic interventions, idiopathy of the subject, and route of administration.

The amount and concentration of administration form in a composition, as well as the quantity of the pharmaceutical composition administered to a subject, can be selected based on clinically relevant factors, the solubility of the administration form in the composition, the potency and activity of the administration form, and the manner of administration of the composition. A composition including a therapeutically effective amount of an administration form disclosed herein, or a pharmaceutically acceptable salt or prodrug thereof, can be administered to a subject for treatment of wounds in a clinically safe and effective manner, including one or more separate administrations of the composition. For example, about 0.05 mg/kg to about 5.0 mg/kg can be administered to a subject per day in one or more doses (e.g., doses of about 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain indications, the total daily dose of administration form can be about 0.05 mg/kg to about 3.0 mg/kg administered to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 mg/kg/day of administration forms using 60-minute QD, BID or TID dosing. In one particular example, pharmaceutical compositions can be administered QD or BID to a subject with, e.g., total daily doses of 1.5 mg/kg, 3.0 mg/kg, 4.0 mg/kg of a composition with up to about 92-98% wt/v.

Additional useful doses can often range from 0.1 to 5 μg/kg or from 0.5 to 1 μg/kg. In other examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly.

In particular embodiments, the compositions described herein can be used in conjunction with other wound treatments. For example, in the case of a diabetic ulcer, sharp debridement, pressure relief, and various methods of infection control may be used.

In various embodiments, a topical formulation of a composition as described herein can be applied to the wound. In some embodiments, a topical formulation is applied superficially and the wound is then covered by a dressing. In particular embodiments, the dressing is moistened. In some embodiments, the dressing can be moistened by saline. In various embodiments, the dressing can be left in place for up to 6 hours, up to 12 hours, or up to 24 hours. In particular embodiments, the dressing is removed, the topical formulation is reapplied, and a new dressing is used to cover the wound.

The compositions disclosed herein can be administered with additional components to reduce the occurrence of unwanted events during wound healing. For example, the compositions described herein can be administered with therapeutics for the treatment of diabetic ulcers such as Becaplermin (e.g., Regranex® (Smith & Nephew, Inc., Memphis, Tenn., USA)).

In various embodiments, the compositions described herein can be administered with antiplatelet medications (e.g. irreversible cyclooxygenase inhibitors, adenosine diphosphate (ADP) receptor inhibitors, phosphodiesterase inhibitors, protease-activated receptor-1 (PAR-1) antagonists, glycoprotein IIB/IIIA inhibitors, adenosine reuptake inhibitors, or thromboxane inhibitors), growth factors (e.g. platelet-derived growth factor (PDGF)), and/or vasodilators.

The compositions can also be administered with anti-infective agents including anthelmintics (e.g., mebendazole), antibiotics including aminoclycosides (e.g., gentamicin, neomycin, tobramycin), antifungal antibiotics (e.g., amphotericin b, fluconazole, griseofulvin, itraconazole, ketoconazole, nystatin, micatin, tolnaftate), cephalosporins (e.g., cefaclor, cefazolin, cefotaxime, ceftazidime, ceftriaxone, cefuroxime, cephalexin), betalactam antibiotics (e.g., cefotetan, meropenem), chloramphenicol, macrolides (e.g., azithromycin, clarithromycin, erythromycin), penicillins (e.g., penicillin G sodium salt, amoxicillin, ampicillin, dicloxacillin, nafcillin, piperacillin, ticarcillin), tetracyclines (e.g., doxycycline, minocycline, tetracycline), bacitracin, clindamycin, colistimethate sodium, polymyxin b sulfate, vancomycin, antivirals (e.g., acyclovir, amantadine, didanosine, efavirenz, foscarnet, ganciclovir, indinavir, lamivudine, nelfinavir, ritonavir, saquinavir, stavudine, valacyclovir, valganciclovir, and zidovudine), quinolones (e.g., ciprofloxacin, levofloxacin), sulfonamides (e.g., sulfadiazine, sulfisoxazole), sulfones (e.g., dapsone), furazolidone, metronidazole, pentamidine, sulfanilamidum crystallinum, gatifloxacin, and sulfamethoxazole/trimethoprim.

Compositions can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

EXEMPLARY EMBODIMENTS

1. A method of promoting wound healing in a subject including topically applying a vector encoding XBP1 and/or IRE-1 to a wound such that the vector infects intact epithelial cells around the wound; and administering tetracycline to stimulate expression of XBP1; thereby promoting wound healing in the subject.
2. A method of promoting epithelialization in a subject in need thereof including up-regulating XBP1 and/or IRE-1 by administering XBP1 and/or IRE-1 in an area where promoting epithelialization would be beneficial, thereby promoting epithelialization in the subject in need thereof.
3. A method of reducing contractures in a subject in need thereof including up-regulating XBP1 and/or IRE-1 by administering XBP1 and/or IRE-1 in an area where reducing contractures would be beneficial, thereby reducing contractures in the subject in need thereof.

In all embodiments, up-regulating can be through administration of a genetic therapy that results in controllable expression of a nucleotide sequence encoding XBP1 and/or IRE-1.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1

Figure 7:
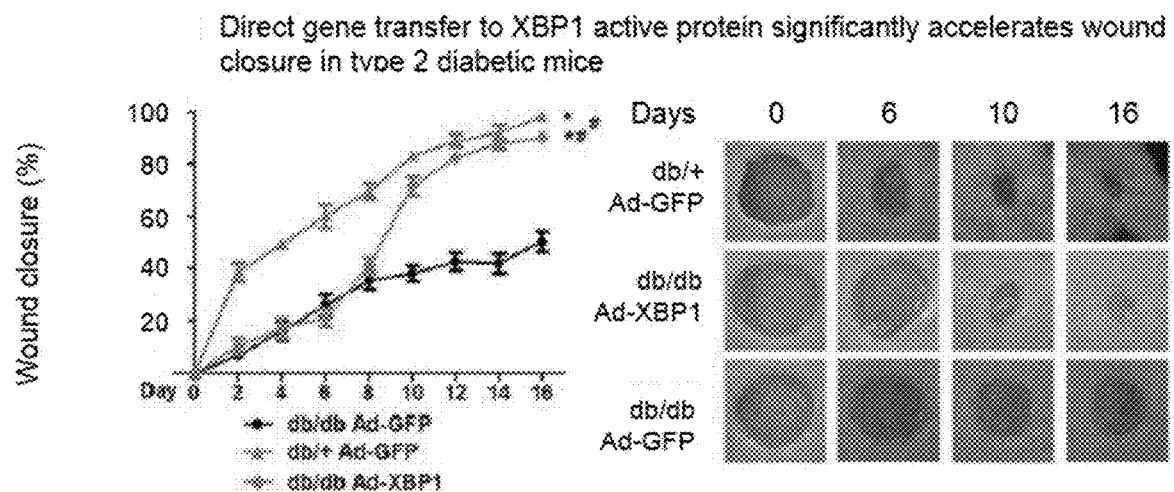
FIG. 7 shows data evidencing that direct gene transfer of XBP1 active protein significantly promotes (e.g., accelerates) wound closure in type 2 diabetic mice.
Figure 8:
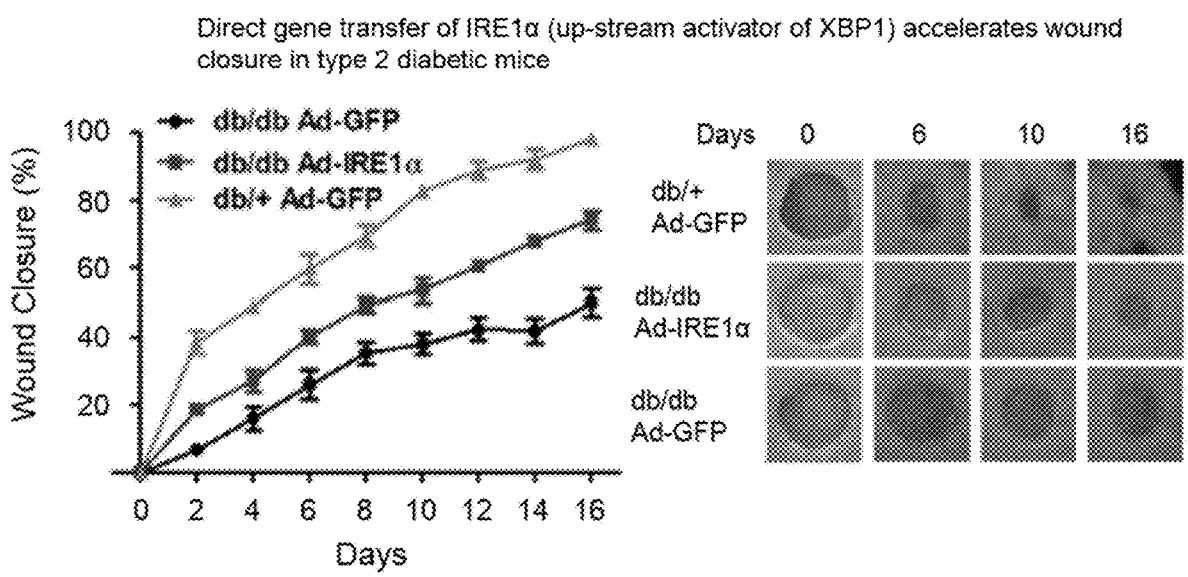
FIG. 8 shows data evidencing that direct gene transfer of IRE1a (up-stream activator of XBP1) promotes (e.g., accelerates) wound closure in type 2 diabetic mice.
Figure 9:
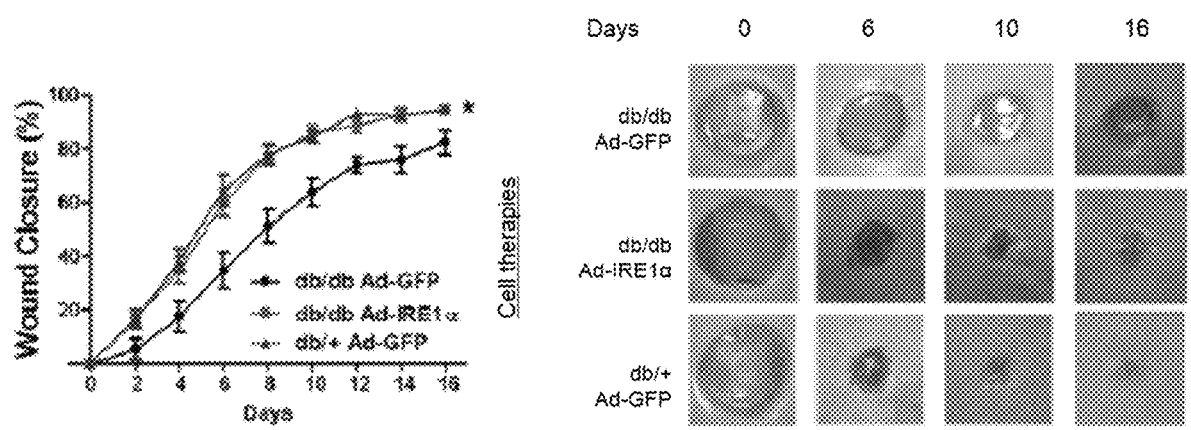
FIG. 9 shows data evidencing that endothelial progenitor cells with IRE1a over-expression significantly promote (e.g., accelerate) wound closure in type 2 diabetic mice.

The following methods were used to collect the data depicted in FIGS. 7-9. Wounds were created on the dorsal surface of the mouse as previously described (Wang et al., *Arteriosclerosis, thrombosis, and vascular biology*. 2014; 34:99-109). The mice were db/db type 2 diabetic mice. The db/+mice served as the normal control. Full-thickness skins were removed using a 6-mm punch biopsy without hurting the underlying muscle. Briefly, 1×10$^8$ particle forming units (pfu) of Ad-IRE1α or Ad-GFP was pre-loaded into the 40 μl PBS at 4° C. Immediately after wounding, the adenovirus suspension was then injected on to the wound edge in the panniculus carnosus layer using a Hamilton syringe and 30% gauge needle. The grouping was as follows: 1) db/+ wound with Ad-GFP; 2) db/db wound with Ad-GFP; 3) db/db wound with Ad-XBP1s; 4) db/db wound with Ad-IRE1a. In db/db wounds receiving cell therapy, 1×10$^6$ bone marrow-derived angiogenic cells (BMACs) with different gene manipulation in 30 μl PBS were topically transplanted onto the wound area immediately after punch. The grouping was as follows: 1) db/db wound with db/+ BMACs transfected with Ad-GFP; 2) db/db wound with db/db BMACs transfected with Ad-GFP; 3) db/db wound with db/db BMACs transfected with Ad-IRE1a. Wounds were covered with transparent oxygen-permeable wound dressing (Bioclusive, Johnson & Johnson). The dressings were changed every other day. Wound closure rates were measured by tracing the wound area onto acetate paper every other day until day 16. The tracings were digitized, and the areas were calculated with a computerized algorithm and converted to percent wound closure (Image J). Wound closure rates were calculated as Percentage Closed (y %)= [(Area on DayoOpen Area on Day,)/Area on Daydx 100, as described in Wang et al., *Arteriosclerosis, thrombosis, and vascular biology.* 2014; 34:99-109. Analgesics were administered, and the mice were monitored daily for food consumption, pain and distress, and general health. In at least some cases, a two-way analysis of variance (ANOVA) with Bonferroni's post hoc analysis was performed with n=5/group, *$p<0.05$ vs. db/db+AD-GFP, and #$p<0.05$ vs. db/+Ad-GFP. The results are depicted in FIGS. 7-9.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in an embodiment's ability to promote wound healing in a diabetic subject.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of promoting healing of an impaired wound in a diabetic subject, the method comprising directly administering immediately after wounding in a single dose, an effective amount of a replication-impaired adenoviral vector comprising a nucleotide sequence encoding human X-box binding protein 1 (XBP1) consisting of the amino acid sequence as set forth in SEQ ID NO: 1 to the wound edge of the diabetic subject, and transiently expressing the XBP1, thereby accelerating wound closure and re-epithelialization of the wound in the diabetic subject.

2. The method of claim 1, further comprising applying a wound dressing to the wound.

3. A method of promoting healing of an impaired wound in a diabetic subject, the method comprising directly administering immediately after wounding in a single dose, an effective amount of a replication-impaired adenoviral vector comprising a nucleotide sequence encoding the amino acid sequence encoding human inositol-requiring enzyme-1α (IRE-1α) as set forth in SEQ ID NO: 2 to the wound edge of the diabetic subject, and transiently expressing the IRE-1α, thereby accelerating wound closure and re-epithelialization of the wound in the diabetic subject.

4. The method of claim 3, further comprising applying a wound dressing to the wound.

5. The method of claim 1, wherein administering comprises injection of the adenoviral vector on to the wound edge.

6. The method of claim 3, wherein administering comprises injection of the adenoviral vector on to the wound edge.

* * * * *